United States Patent
Mitre et al.

(10) Patent No.: US 10,213,495 B2
(45) Date of Patent: Feb. 26, 2019

(54) **METHODS OF TREATING ALLERGIES AND AUTOIMMUNE DISEASES WITH HOMOGENATE OF AXENIC *C. ELEGANS***

(71) Applicant: The Henry M. Jackson Foundation for the Advancement of Military Medicine, Inc., Bethesda, MD (US)

(72) Inventors: Edward E. Mitre, Rockville, MD (US); Marina Torrero, Fairfax, VA (US); Belinda Jackson, Burtonsville, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 245 days.

(21) Appl. No.: 15/036,982

(22) PCT Filed: Nov. 19, 2014

(86) PCT No.: PCT/US2014/066320
§ 371 (c)(1),
(2) Date: May 16, 2016

(87) PCT Pub. No.: WO2015/077288
PCT Pub. Date: May 28, 2015

(65) Prior Publication Data
US 2016/0271235 A1  Sep. 22, 2016

Related U.S. Application Data

(60) Provisional application No. 61/906,739, filed on Nov. 20, 2013.

(51) Int. Cl.
*A61K 39/00* (2006.01)
*A61K 35/62* (2006.01)
*A61K 39/35* (2006.01)
*A61K 39/39* (2006.01)

(52) U.S. Cl.
CPC .......... *A61K 39/0003* (2013.01); *A61K 35/62* (2013.01); *A61K 39/0008* (2013.01); *A61K 39/35* (2013.01); *A61K 39/39* (2013.01); *A61K 2039/55516* (2013.01)

(58) Field of Classification Search
None
See application file for complete search history.

(56) References Cited

U.S. PATENT DOCUMENTS

2010/0303721 A1    12/2010   Weinstock et al.

OTHER PUBLICATIONS

Ajendra, J., et al. Clin. Immunol. 2016;164:119-122.*
Kim et al., "Crude extracts of Caenorhabditis elegans Suppress Airway Inflammation in a Murine Model of Allergic Asthma", PLoS one, Apr. 2012 vol. 7, Issue 4, e35447, pp. 1-10.
Zaccone et al., "Schistosoma mansoni egg antigens induce Treg that participate in diabetes prevention in NOD mice", European Journal of Immunology, 2009, vol. 39, No. 4, pp. 1098-1107.
Zaccone et al., "The S. mansoni glycoprotein ω-1 induces Foxp3 expression in NOD mouse CD4⁺ T cells", European Journal of Immunology, 2011, vol. 41, No. 9, pp. 2709-2718.
Stone et al., "IgE, Mast Cells, Basophils, and Eosinophils", Journal of Allergy and Clinical Immunology, Feb. 2010, vol. 125, No. 2, pp. S73-S80.

* cited by examiner

*Primary Examiner* — G. R. Ewoldt
(74) *Attorney, Agent, or Firm* — MH2 Technology Law Group, LLP

(57) ABSTRACT

Methods of using axenic *C. elegans* homogenate for treating allergies or an autoimmune disease are disclosed. Also disclosed is a composition comprising a homogenate of *C. elegans*, wherein the homogenate is obtained from *C. elegans* cultured in axenic media, for use in treating an allergy or autoimmune disease.

14 Claims, 6 Drawing Sheets

METHODS OF TREATING ALLERGIES AND AUTOIMMUNE DISEASES WITH HOMOGENATE OF AXENIC *C. ELEGANS*

CROSS REFERENCE TO RELATED APPLICATIONS

This application is a U.S. National Stage application of PCT/US2014/066320 filed 19 Nov. 2014, which claims the benefit of, and relies on the filing date of, U.S. provisional patent application No. 61/906,739, filed 20 Nov. 2013, the entire disclosure of which is incorporated herein by reference.

STATEMENT OF GOVERNMENT INTEREST

This invention was made with government support under grant number DK083131 awarded by the National Institutes of Health. The government has certain rights in this invention.

BACKGROUND

The disease burden of the more than 80 distinct autoimmune diseases in the United States is enormous, collectively affecting 14 to 22 million people, an estimated 5-8% of the U.S. population. In addition, an estimated 50 million people in the U.S. suffer allergies. Allergy is the fifth leading chronic disease in the U.S. among all ages, and the third most common chronic disease among children under 18 years old.

Several types of medications are available to treat allergies symptoms, including antihistamines, decongestants, corticosteroids, and others. It is estimated that the annual cost for prescription and over-the-counter medications in the U.S. to treat allergies is $11 billion.

For most autoimmune diseases, immunosuppression is the therapy of choice. Conventional agents that induce non-specific immunosuppression, such as non-steroidal anti-inflammatory drugs, glucocorticoids, and methotrexate have traditionally been the mainstay of therapy for many autoimmune diseases. While helpful, these medications are not always fully efficacious and are associated with significant toxicity when used chronically. Additionally, by non-specifically suppressing the immune system, these medications substantially increase patient susceptibility to infections.

Over the past few years, a number of new medications have become available which are able to specifically target certain arms of the immune response. While such approaches clearly represent a step forward in focusing immunosuppressive therapy, none does so in an antigen-specific manner. Consequently, these new medications still increase patient susceptibility to infections, albeit to a smaller range of organisms than non-specific immunosuppressive agents. This phenomenon is exemplified by the recent findings that tumor necrosis factor inhibitors, despite blocking the activity of only one cytokine, increase the risk of pneumonia, severe skin infections, and reactivation of prior tuberculosis.

Given the increased risk to infection that occurs when even specific facets of the immune system are inhibited, an alternative therapy for autoimmune diseases would be one that suppresses only self-reactive immune responses. Such a therapy would, ideally, be efficacious without compromising the body's ability to fight off infections. Several autoimmune diseases appear to be caused in large part by Th1-driven inflammation. Examples include type 1 diabetes, multiple sclerosis, Crohn's disease, inflammatory bowel disease, rheumatoid arthritis, and posterior uveitis. While the Th1/Th2 paradigm has evolved somewhat since its first description in 1986, it is still generally accepted that Th1 and Th2 responses have the ability to counter regulate each other. In particular, IL-4 suppresses differentiation of naïve T-cells into Th1 cells, resulting in decreased Th1 cytokine production and decreased Th1 cell proliferation in response to Th1-inducing antigens. In addition to Th2 responses, immunoregulatory networks can also suppress Th1 responses. These mechanisms include downregulatory cytokines such as IL-10 and TGFb, and regulatory cells such as T-regulatory cells and B-regulatory cells. Thus, there is a need for new treatment modalities that selectively down regulate Th1 responses.

Other therapies have also become available which use exposure to parasitic worms to treat or prevent hyperinflammatory diseases. To date, two types of parasitic worm-mediated therapy have been used in human clinical trials—*Trichuris suis* (pig whipworm) to treat ulcerative colitis and Crohn's disease, and live hookworm to treat allergies. While the exact mechanism(s) by which parasitic worms protect against inflammatory diseases is not completely understood, evidence suggests that parasitic worms induce strong immunoregultory signals. Patients exposed to parasitic worms demonstrated increased IgE antibody levels, increased numbers of circulating basophils and eosinophils, and increased IL-10 production which can suppress excessive inflammatory responses.

However, a number of factors have limited the widespread use of parasitic worm infections in commercial therapeutic applications. Not only might patients potentially express concern about being infected with parasitic worms, but if so infected, they incur the risk of suffering from pathology induced by live worm infection. Additionally, the use of animal hosts to cultivate parasitic worms can compromise batch purity and homogeneity during production. Due to the complex life cycle of parasitic worms, it is also often difficult to obtain sufficiently large quantities of antigen necessary for commercial therapeutic applications. Thus, there is also a need for new treatment modalities that can suppress excessive inflammatory responses without the risks associated with parasitic infections.

SUMMARY

The present disclosure provides methods of treating an allergy or autoimmune disease by administering to a subject a composition comprising *Caenorhabditis elegans* (*C. elegans*) or a homogenate thereof containing *C. elegans* antigens, where the *C. elegans* has been cultured in axenic media. *C. elegans* is a non-parasitic, free living nematode that is non-pathogenic to humans. Administering axenic *C. elegans* antigen activates basophils and eosinophils, increases IgE antibody levels, and increases production of IL-10. Without intending to be bound by any theory, activated basophils and eosinophils may protect against Th1-mediated autoimmune disease, for example, through the release of histamine or the synthesis of IL-4 and/or IL-10, all of which have been shown to counteract or suppress Th1-driven immune responses, or through the induction of negative feedback pathways that down regulate immune responses.

One embodiment is directed to a method of treating an allergy or an autoimmune disease in a subject, the method comprising administering to the subject an effective amount of a composition comprising a homogenate of *C. elegans*, wherein the homogenate is obtained from *C. elegans* cultured in axenic media.

Another embodiment is directed to a method of increasing levels of IgE antibody in a subject, the method comprising administering to the subject an effective amount of a composition comprising a homogenate of *C. elegans*, wherein the homogenate is obtained from *C. elegans* cultured in axenic media.

A further embodiment is directed to a method of increasing levels of IL-10 in a subject, the method comprising administering to the subject an effective amount of a composition comprising a homogenate of *C. elegans*, wherein the homogenate is obtained from *C. elegans* cultured in axenic media.

In yet another embodiment, the autoimmune disease can be a Th-1 mediated autoimmune disease. In a further embodiment, the Th1-mediated autoimmune disease is selected from type 1 insulin-dependent diabetes mellitus, scleroderma, multiple sclerosis, posterior uveitis, Crohn's disease, inflammatory bowel disease, and rheumatoid arthritis.

In a further embodiment, the allergy can be environmental allergies and/or asthma.

In an embodiment, the subject is a mammal, preferably a human.

In an embodiment, the composition is administered orally, parenterally, or subcutaneously.

In yet another embodiment, the composition is free of *E. coli* endotoxins. In a further embodiment, the composition is free of lipopolysaccharides.

In another embodiment, the composition comprising axenic *C. elegans* homogenate is administered chronically to the subject. In one embodiment, the chronic administration comprises administering the composition with axenic *C. elegans* homogenate to the subject every week for at least 20 weeks. In another embodiment, the chronic administration comprises administering the composition with axenic *C. elegans* homogenate to the subject one or more times a day for at least 5, 7, or 10 days.

Another aspect is directed to a composition comprising axenic *C. elegans* homogenate for use in therapy. In one embodiment the composition comprises axenic *C. elegans* homogenate for use in treating an autoimmune disease, including a Th1-mediated autoimmune disease, such as type 1 insulin-dependent diabetes mellitus, scleroderma, multiple sclerosis, posterior uveitis, Crohn's disease, inflammatory bowel disease, and rheumatoid arthritis. In another embodiment, the composition comprises axenic *C. elegans* homogenate for use in treating allergies, including environmental allergies and asthma. The composition optionally comprises a pharmaceutically acceptable excipient.

BRIEF DESCRIPTION OF THE DRAWINGS

The accompanying drawings, which are incorporated in and constitute a part of this specification, illustrate certain embodiments, and together with the written description, serve to explain certain principles of the antibodies and methods disclosed herein.

FIG. 1 shows percentages of circulating white blood cells that are eosinophils (A) and basophils (B) in mice after receiving 24 intraperitoneal injections of 100 µg of axenic *C. elegans* antigen or phosphate buffered saline as control over a period of 12 weeks. Statistical significance between groups was assessed by the Mann-Whitney test (*<0.05).

DETAILED DESCRIPTION

Figure 1A:
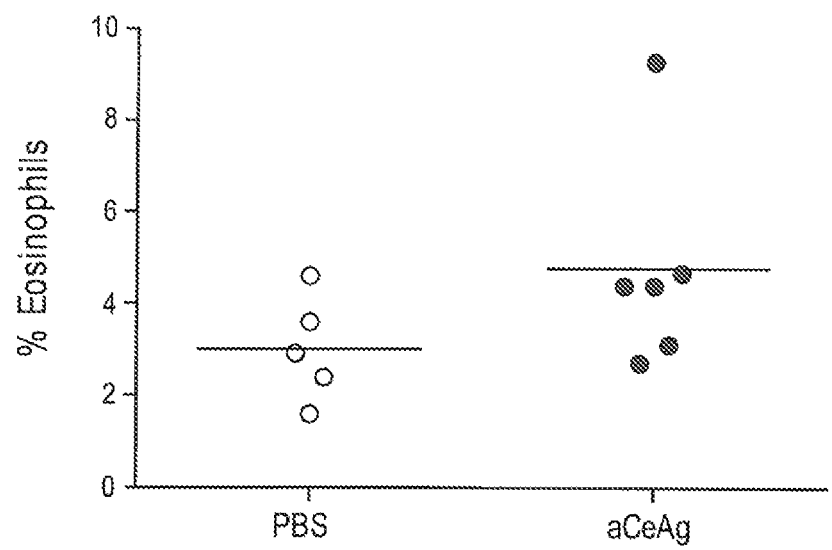
FIGS. 1A-B: Effects of axenic *C. elegans* antigen injections in vivo.

Reference will now be made in detail to various exemplary embodiments, examples of which are illustrated in the accompanying drawings. It is to be understood that the following detailed description is provided to give the reader a fuller understanding of certain embodiments, features, and details of aspects of the invention, and should not be interpreted as a limitation of the scope of the invention.

1. Definitions

In order that the present invention may be more readily understood, certain terms are first defined. Additional definitions are set forth throughout the detailed description.

The term "axenic media" as used in this disclosure refers to culture media for growing *Caenorhabditis elegans* that does not contain *Escherichia coli*. Thus, an axenic homogenate of *C. elegans* is a homogenate obtained from *C. elegans* cultured in axenic media.

The term "effective amount" refers to a dosage or amount that is sufficient for treating an indicated disease or condition.

The terms "treatment" or "treating" and the like refer to any treatment of any disease or condition in a mammal, e.g. particularly a human or a mouse, and includes inhibiting a disease, condition, or symptom of a disease or condition, e.g., arresting its development and/or delaying its onset or manifestation in the patient or relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans.

The term "pharmaceutically acceptable carrier" or "pharmaceutically acceptable excipient" means solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art.

As understood in the art, the term "Th1-mediated autoimmune disease" means an autoimmune disease that is associated with a type 1 helper T cell (Th1) response. Such diseases include, but are not limited to, type 1 insulin-dependent diabetes mellitus, scleroderma, multiple sclerosis, posterior uveitis, Crohn's disease, inflammatory bowel disease, and rheumatoid arthritis.

The term "chronically administered" or the like means that the composition is administered to the subject at least as frequently as once a week for at least 10 weeks or at least as frequently as one or more times a day for at least 5 days.

2. Th1/Th2 Immune Responses

CD4 T helper cell responses to antigens can be classified based on the cytokines they produce. Type 1 helper T cells (Th1) produce inflammatory cytokines, such as IFN-γ, IL-2, TNF-α, and TNF-β. Th1 cells activate macrophages and are associated with cell-mediated immune responses. Type 2 helper cells (Th2), on the other hand, typically produce cytokines, such as IL-4, IL-5, IL-10, and IL-13. Th2 cells activate B cells and are associated with antibody-mediated immune responses.

3. Autoimmune Diseases and Allergies

Autoimmune diseases are characterized by overactive immune responses to self antigens expressed on cells. In essence, the immune system mistakes a self antigen in the body as a pathogen and mounts an attack against the cell or tissue expressing the self antigen. Autoimmune diseases usually involve chronic autoimmune responses, leading to long-term tissue damage. Several autoimmune diseases appear to be caused in large part by Th1-driven inflammation based, in part, on cytokine profiles, including predominantly high levels of IFN-γ. Examples of Th1-mediated autoimmune diseases, include, but are not limited to, type-1 insulin-dependent diabetes mellitus, multiple sclerosis, Crohn's disease, inflammatory bowel disease, rheumatoid arthritis, and posterior uveitis.

Allergic reactions occur when a body's immune system reacts to normally harmless substances in the environment. Allergies usually involve excessive activation of mast cells and basophils by IgE. This results in an inflammatory response which can range from uncomfortable to life-threatening anaphylaxis.

4. Axenic *C. elegans* Homogenate Therapy for Autoimmune Diseases and Allergies The prevalence of allergies, type 1 diabetes, and other autoimmune diseases has increased sharply over the past few decades. While genetic factors play a role in susceptibility to type 1 diabetes, the dramatic worldwide increase in the prevalence of type 1 diabetes is probably due to changes in environmental factors.

One environmental change that may play a part in the recent increase in autoimmune diseases is the loss of chronic parasitic worm infections in developed countries. Multiple studies have found that individuals infected with chronic parasitic worm infections have lower rates of autoimmune diseases than others living in the same environment. Experimentally, parasitic worms have been shown to protect against type 1 diabetes and other autoimmune diseases in several animal models. In humans, oral administration of porcine whipworm eggs has been shown to protect against inflammatory bowel disease.

Until recently, most people had lifelong infections with parasitic worms. As helminths have been identified in neolithic and pre-Columbian mummies, it is likely that the human immune system evolved in the setting of chronic infection with these parasites. Consequently, it has been posited that the loss of parasitic worm infections is partially responsible for the increased prevalence of autoimmune and allergic diseases in developed countries—the notion being that now, in the absence of the immunomodulatory responses triggered by helminths, our immune systems have become hyperresponsive.

Unlike most bacterial or viral pathogens, helminth infections induce the production of specific IgE. This IgE binds to basophils and mast cells through the Fc epsilon receptor I (FcεRI), the high affinity IgE receptor. Helminth specific antigens can then activate basophils and mast cells by cross-linking IgE molecules and aggregating FcεRIs. As helminths are large organisms that release substantial amounts of antigen, and as these infections last for years, helminth infections likely induce a state of chronic basophil and mast cell activation. Indeed, recent time course studies in our lab demonstrate that both chronic basophil activation and chronic mast cell activation occur during infection of mice with the filarial nematode *Litomosoides sigmodontis*.

Helminth infections also induce production of the cytokine IL-10. IL-10 is an anti-inflammatory cytokine that was initially described as a Th2-type or Treg-type cytokine but it is now known that IL-10 is more broadly expressed. IL-10 acts as a crucial feedback regulator of diverse immune responses, including Th1-mediated and Th2-mediated immune responses.

Without intending to be bound by any theory, there are at least two likely mechanistic rationales for postulating that chronic activation of basophils and mast cells may protect against Th1-driven autoimmune disease. First, factors released by basophils and mast cells may have direct immunomodulatory properties that are protective against Th1-mediated autoimmune diseases. Basophils, for example, release large quantities of IL-4 when activated and have been shown to do so in response to parasite antigen in filaria-infected patients as well as in animal models of helminth infection. As destruction of β-islet cells in type 1 diabetes is driven by IFN-γ release from Th1 cells, and as IL-4 counter regulates Th1 responses and has been shown to improve Th1-driven autoimmune diseases, chronic basophil activation may protect against type 1 diabetes by release of IL-4. Similarly, histamine, which is released from both basophils and mast cells, has been shown in vitro to suppress Th1 responses by signaling through the H2 receptor on lymphocytes. Alternatively, chronic activation of basophils and mast cells could induce negative feedback pathways that tamp down ongoing autoimmune responses. Interestingly, there is substantial evidence that chronic immunotherapy, in which patients with IgE-mediated allergies are given weekly injections of allergen, augments immune regulatory networks such as the suppressive cytokine IL-10 and natural T-regulatory cells.

To determine whether recapitulation of the IgE-mediated immune responses induced by helminths can afford protection against autoimmunity in the absence of actual infection, non-obese diabetic (NOD) mice were repeatedly administered intraperitoneal injections of axenic *C. elegans* homogenate. NOD mice spontaneously develop type 1 diabetes (also known as insulin dependent diabetes mellitus), a form of diabetes that develops from the autoimmune destruction of the insulin-producing beta islet cells of the pancreas. NOD mice are an art recognized animal model for type 1 diabetes.

To mimic chronic helminth in vivo without using live parasitic worms, NOD mice were treated with twice weekly injections of axenic *C. elegans* homogenate. Treated mice exhibited increases in circulating basophils, eosinophils, total IgE, and *C. elegans*-specific IgE. These immunologic changes are consistent with those observed in chronic helminth infections. Additionally, splenocytes of *C. elegans*-treated mice released substantial quantities of the downregulatory cytokine IL-10, whereas those from control-treated mice did not. Consistent with our hypothesis, mice given axenic *C. elegans* antigen injections were significantly protected from developing autoimmune diabetes (10% disease rate vs 80% in controls) and exhibited less inflammation in the pancreatic islets.

These results demonstrate that axenic *C. elegans* homogenate therapy can protect against the onset of type I diabetes in NOD mice and suggests that repeated administration of axenic *C. elegans* homogenate represents a new avenue of therapy for Th1-associated autoimmune diseases.

6. Axenic Media

This disclosure provides a composition comprising a homogenate of *C. elegans*, wherein the homogenate is obtained from *C. elegans* cultured in axenic media, for use in treating allergies and autoimmune diseases, such as type 1 diabetes. *C. elegans* is commonly cultured on Nematode Growth Medium (NGM) agar using *E. coli* as a food source. However, this method of culturing *C. elegans* introduces undesirable *E. coli* endotoxins into the end homogenate. *E. coli* endotoxin, including lipopolysaccharides (LPS), is extremely difficult to eliminate through purification methods. Yet if endotoxin is not eliminated in the homogenate that is administered to a subject, the endotoxin will trigger an undesirable immune response, such as increased IFNγ production.

Axenic media for culturing *C. elegans* can include various salt solutions, essential amino acids, non-essential amino acids, vitamins and growth factors, nucleic acid substitutes, and energy sources, as described in "Chemically defined medium and *Caenorhabditis elegans*," Szewczyk et al., *BMC Biotechnology* 2003, 3:19, which is hereby incorporated by reference in its entirety. The axenic media can further include hemin chloride, preferably 20 uM hemin chloride; ultra-pasteurized (UHT) skim milk, preferably 10-20% UHT skim milk; cholesterol, preferably 5 ug/mL cholesterol; and antibiotics, preferably tetracycline, streptomycin, and nalidixic acid, more preferably 100 to 250 ug of tetracycline, streptomycin, and nalidixic acid. Addition of heme and cholesterol enhances worm growth, as *C. elegans* worms need to obtain heme and cholesterol from the environment ("Lack of heme synthesis in a free-living eukaryote", Rao et al. *PNAS* 2005, 102:12, "The requirement of sterol and various sterol precursors in free-living nematodes", N. C. Lu, et al., *Nematologica* 1977, 23:57-61).

7. Methods of Making Axenic *C. elegans* Homogenate

*C. elegans* can be grown in axenic media as described above. Whole *C. elegans* worms can be pulverized in solution by methods known in the art. The pulverized worms can then be centrifuged and the supernatant decanted and saved using methods known in the art. Optionally, the pellet can be resuspended and centrifuged. Centrifugation and supernatant decanting/saving can be repeated as many times as necessary or desired. Saved supernatants can be combined to form the final homogenate composition comprising axenic *C. elegans* antigen.

8. Methods of Use

The axenic *C. elegans* homogenate described herein can be used in a variety of research and medical applications. In one aspect, the disclosure provides a method of treating an allergy or autoimmune disease in a subject, comprising administering to said subject an effective amount of a composition comprising a homogenate of *C. elegans*, wherein the homogenate is obtained from *C. elegans* cultured in axenic media. The composition can further include a pharmaceutically acceptable carrier and other excipients. In certain embodiments, the composition includes at least one non-naturally occurring pharmaceutically acceptable carrier or other excipient. Preferably, the composition is one that does not occur in nature. Preferably, the autoimmune disease is a Th1-mediated autoimmune disease, including, but not limited to type-1 insulin-dependent diabetes mellitus, multiple sclerosis, Crohn's disease, inflammatory bowel disease, rheumatoid arthritis, and posterior uveitis.

9. Formulations and Administration

The disclosure provides compositions comprising a homogenate of *C. elegans*, wherein the homogenate is obtained from *C. elegans* cultured in axenic media. In certain embodiments, the compositions are suitable for pharmaceutical use and administration to patients. These compositions comprise an axenic homogenate of *C. elegans* and a pharmaceutically acceptable excipient. The compositions may also contain other active compounds providing supplemental, additional, or enhanced therapeutic functions. Preferably, the composition is one that does not occur in nature. The pharmaceutical compositions may also be included in a container, pack, or dispenser together with instructions for administration. In one embodiment, the composition comprises an axenic homogenate of *C. elegans* for use in treating an autoimmune disease, including a Th1-mediated autoimmune disease, such as type-1 insulin-dependent diabetes mellitus, multiple sclerosis, Crohn's disease, inflammatory bowel disease, rheumatoid arthritis, and posterior uveitis.

A pharmaceutical composition of the invention is formulated to be compatible with its intended route of administration. Methods to accomplish the administration are known to those of ordinary skill in the art. This includes, for example, injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically contemplated, by such means as depot injections or erodible implants. Localized delivery is particularly contemplated, by such means as delivery via a catheter to one or more arteries, such as the renal artery or a vessel supplying a localized tumor. The composition can also be admixed with food as a food additive.

In one embodiment a composition including axenic *C. elegans* homogenate is administered to a patient by injection (e.g., intraperitoneally, intravenously, subcutaneously, intramuscularly, etc.). The composition may be administered, for example, by bolus injunction or by slow infusion. Slow infusion over a period of 30 minutes to 2 hours may be used. Generally, an initial candidate dosage can be about 5-100 µg/kg (0.005-0.1 mg/kg). A typical daily dosage might range from about any of 0.001 mg/kg to about 100 mg/kg; about 0.01 mg/kg to about 10 mg/kg; or about 0.1 mg/kg to about 5 mg/kg. The appropriate dosage of the axenic *C. elegans* homogenate will depend on various factors, including the type of axenic *C. elegans* homogenate used (or compositions thereof), route of administration, frequency of administration, patient's health, age, or size, the type and severity of the disease to be treated, whether the agent is administered for preventive or therapeutic purposes, previous therapy, the patient's clinical history and response to the antibody, and the discretion of the attending physician. Typically, the clinician will administer the axenic *C. elegans* homogenate until a dosage is reached that achieves the desired result.

For repeated administrations over several days or longer, depending on the condition, the treatment is sustained until a desired suppression of symptoms occurs or until sufficient therapeutic end points are achieved. An exemplary dosage regimen comprises administering a daily dose of about 5-100 µg/kg for about 5-14 days (or longer), with or without weekly maintenance doses of about 100-250 µg/kg. Alternatively, an exemplary dosing regimen comprises administering an initial dose of about 5-100 µg/kg, followed by a weekly maintenance dose of about 5-250 µg/kg of the axenic *C. elegans* homogenate, or followed by a maintenance dose of about 5-250 µg/kg every other week. However, other dosage regimens may be useful, depending on the pharmacokinetic parameters that the practitioner wishes to achieve. For example, dosing from one to four times a week is contemplated. In some embodiments, dosing frequency is once every day, every other day, every third day, every fourth day, every fifth day, every sixth day; once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays.

The dosing regimen can also vary over time. One risk of axenic *C. elegans* homogenate therapy is the induction of anaphylaxis, resulting from chronic mast cell and basophil activation. To reduce this risk, it is possible to initiate treatment with smaller doses of axenic *C. elegans* homogenate followed by a gradual increase in treatment dosage. Such an approach would be similar to allergen immunotherapy, where the allergen dose is gradually increased over time. Allergen immunotherapy induces repeated basophil and mast cell activation and is routinely conducted in the outpatient arena for diseases as benign as allergic rhinitis. Thus, in one embodiment, the axenic *C. elegans* homogenate therapy can be administered at a smaller initial dose followed by gradually increasing doses. The particular dosage regimen, i.e., dose, timing and repetition, will depend on the particular individual and that individual's medical history, as well as the properties of the axenic *C. elegans* homogenate.

Toxicity and therapeutic efficacy of the composition can be determined by standard pharmaceutical procedures in cell cultures or experimental animals, e.g., determining the $LD_{50}$ (the dose lethal to 50% of the population) and the $ED_{50}$ the dose therapeutically effective in 50% of the population). The dose ratio between toxic and therapeutic effects is the therapeutic index and it can be expressed as the ratio $LD_{50}/ED_{50}$. Axenic *C. elegans* homogenates that exhibit large therapeutic indices may be less toxic and/or more therapeutically effective.

To test whether repeated administration of axenic *C. elegans* antigen (aCeAg) can protect against a Th1-driven autoimmune disease, the effects of repeated aCeAg injections on the development of type 1 diabetes in the NOD mouse model were studied. The studies demonstrate that aCeAg delays type 1 diabetes onset and decreases autoimmune inflammation against insulin-producing cells Immunological tests demonstrate that aCeAg injections induce immunologic changes similar to those observed in chronic helminth infections, with increases in IgE, eosinophils, basophils, and IL-10 production. Further, in vitro testing demonstrates that aCeAg, in contrast to soluble antigen prepared from *C. elegans* worms grown on *E. coli* plates, does not induce TLR4 activation.

Material & Methods

Mice: Female NOD and IL-4-deficient NOD.129P2(B6)-Il4$^{tm1Cgn}$/DvsJ mice (The Jackson Laboratory, Bar Harbor, Me.) were maintained at the Uniformed Services University (USU) animal facility with free access to food and water. All experiments were performed under protocols approved by the USU Institutional Animal Care and Use Committee.

Assessment of diabetes: Glucose levels of mice were determined from blood taken by orbital bleeds every other week using a standard blood glucose meter (Accu-Check® Advantage, Roche Diagnostics GmbH). Mice with glucose levels greater than 230 mg/dl in two consecutive measurements were considered diabetic.

Preparation of axenic *C. elegans* antigen: *C. elegans* worms were grown in chemically defined axenic media. The axenic media included all the ingredients listed by Szewczyk and colleagues [1], plus 20 mM of hemin chloride, 15% ultra-pasteurized skim milk, 5 mg/ml cholesterol, 100 mg/ml tetracycline, 250 mg/ml streptomycin, and 250 mg/ml nalidixic acid. Whole *C. elegans* worms are then mechanically homogenized by placing into "D" tubes from BioPulverizer System 1 (MP Biomedicals) and then run on a FastPrep-24 system (MP Biomedicals) at 4M/s$^2$ for 20 s. Samples were then centrifuged at 16, 100 g for 1 min, supernatant saved, and the pellet resuspended in another 1 ml PBS. The fast-prep run, centrifugation, and removal of supernatant were then repeated on the resuspended pellet. Saved supernatants were combined, centrifuged at 15,000 g for 5 min, and the final supernatant used as aCeAg. Final protein concentration was determined using the Pierce BCA Protein Assay Kit.

Treatment with axenic *C. elegans* antigen: Beginning at 7 weeks of age, mice were given twice weekly i.p. injections of 100 µg aCeAg or PBS as control until 17 weeks of age, at which point they received one injection per week until study endpoint at 20 weeks. Animals were euthanized at 20 weeks of age to assess pancreas inflammation, splenocyte cytokine production, and circulating IgE, basophil, and eosinophil levels.

Assessment of pancreas inflammation: Pancreases were isolated and fixed in 10% formalin. Haematoxylin-eosin stained slices were assessed for inflammation by a pathologist blinded to the intervention group. Total numbers of islets of three longitudinal sections 400 µm apart of each pancreas were assessed. The severity of insulitis was scored as non-infiltrated, periinsulitis (lymphocytes at the periphery of islets), or intrainsulitis (lymphocyte infiltration into the interior of the islets lesser or greater than 50%).

Spleen cell culture: At study endpoint animals were euthanized and spleens were isolated. Spleen cells were prepared and cultured. In brief, single cell suspensions were obtained, red blood lysis performed for spleen cells (ACK Lysing Buffer, Quality Biological, Inc., Gaithersburg, Md.), and cells were plated at a concentration of $2\times10^6$ cells/ml in enriched media (Iscove's Dulbecco modified medium (Mediatech, Manassas, Va.) including 10% fetal calf serum (Valley Biomedical, Winchester, Va.), 1% L-glutamine (Mediatech, Gaithersburg, Md.), 1% insulin-transferrin-selenium medium (Invitrogen Inc., Carlsbad, Calif.) and 80 µg/ml gentamicin (Quality Biological, Inc., Gaithersburg, M stimulated with PBS as control or 20 µg/ml aCeAg, and cultured at 37° C., 5% $CO_2$.

Measurement of cytokines by ELISA: Cytokine enzyme-linked immunosorbent assays (ELISAs) were performed from spleen cell cultures. Culture supernatants from cells that were cultured as described above were collected after 72 h of incubation. IFN-γ, IL-4, IL-5, and IL-10 were quantified according to the manufacturer's instructions (BD Biosciences, Franklin Lake, N.J.).

Measurement of total and aCeAg-specific IgE levels by ELISA: Blood was collected from aCeAg or PBS treated NOD mice at study endpoint immediately after euthanasia by cardiac puncture and analyzed for total and aCeAg-specific IgE by colorimetric sandwich ELISA. Flat-bottom Immulon 4 plates (Thomas Scientific, Swedesboro, N.J.) were coated overnight at 4° C. with 10 mg/ml anti-mouse IgE (clone R35-72) for total IgE or 20 mg/ml aCeAg for aCeAg-specific IgE. Blocking was performed by 1 h incubation of plates with 5% bovine serum albumin in PBS. Prior to testing, IgG was adsorbed from serum samples by incubation of serum with GammaBind G Sepharose (Amersham Biosciences, Uppsala, Sweden) overnight at 4° C. Serum samples were then diluted 1:5 and 1:50 for total IgE measurements. Plates were washed and incubated with biotinylated rat anti-mouse IgE (clone R35-118) in PBS. Following washing, 1/1000 dilution of alkaline phosphatase-conjugated streptavidin (BD Pharmingen) was added, and plates were incubated for 1 h at 37° C. Nitrophenyl phosphate disodium (Sigma-Aldrich, St. Louis, Mo.) was used as substrate. Purified mouse IgE was used as standard for total IgE (BD Biosciences). For aCeAg-IgE measurements, samples from control and experimental groups were analyzed as duplicates on the same plate to allow for accurate comparison between groups by OD. Absorbance was detected at 405 nm using a PerkinElmer Victor3 V microplate reader (PerkinElmer, Waltham, Mass.). All samples were analyzed as duplicates at the same time on the same plate to allow accurate comparison between groups by OD.

Flow cytometric detection of basophils and eosinophils: Whole blood (100 ml) obtained by cardiac puncture after animal euthanasia at 20 weeks was aliquotted in 5 ml polypropylene round-bottom tubes (BD Falcon). Red blood cells were lysed and leukocytes fixed with whole blood lysing reagent (Beckman Coulter, Galway, Ireland). Cells were washed twice with 2 ml of PBS and centrifuged at 500×g for 5 min Supernatants were aspirated and cells resuspended in 100 ml of 1% bovine serum albumin/PBS followed by incubation at 4° C. for 1 h. Cells were stained with anti-IgE FITC (R35-71), anti-CD4 PerCP (RM4-5) and anti-B220 PerCP (RA3-6B2) to identify basophils; or SiglecF PE(E50-2440), CD45 FITC (30-F11) and CD11c APC (HL3) to identify eosinophils. All the antibodies were purchased from BD Pharmingen. Cells were washed and resuspended in 200 ml of PBS for analysis using a BD LSR II Optical Bench flow cytometer.

Statistics: Statistical analyses were performed with GraphPad Prism software (GraphPad Software). Differences between two unpaired groups were tested for significance with the Mann-Whitney-U-test. P-values <0.05 were considered significant. All experiments were performed at least twice.

Figure 1B:
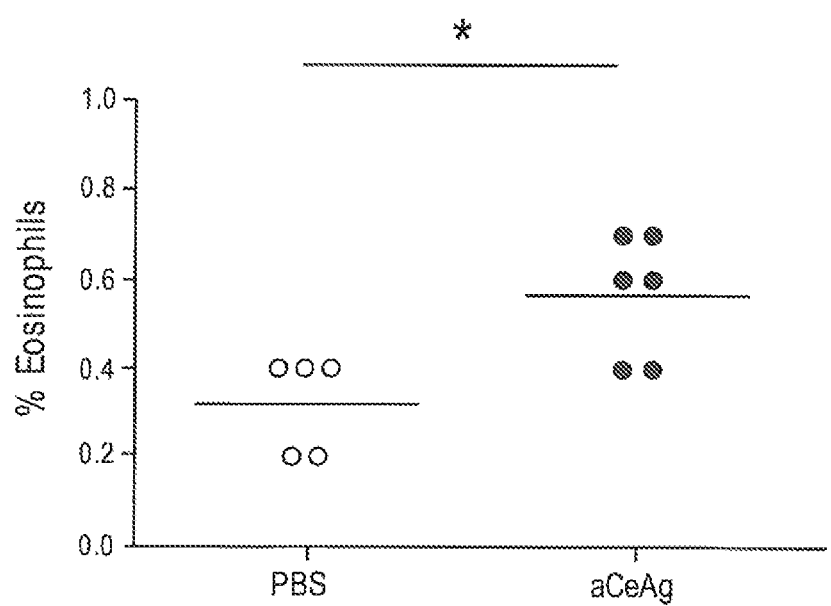
Figure 2A:
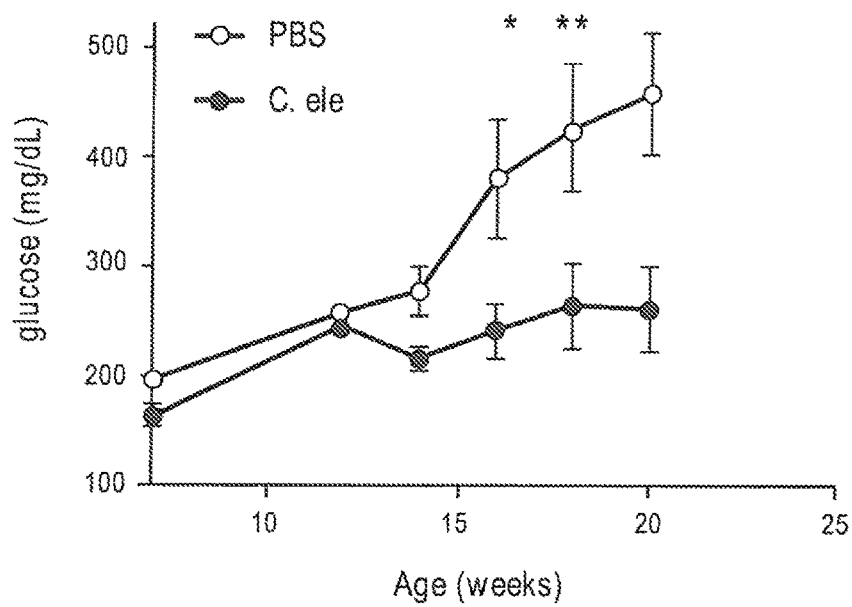
FIGS. 2A-C: Treatment with axenic *C. elegans* antigen delays the onset of diabetes. (A) Mean blood glucose levels and (B) percentages of NOD mice with diabetes during treatment with twice weekly injections of 100 µg axenic *C. elegans* antigen (n=10) or PBS control (n=10). (C) Mean total numbers of pancreatic islets from axenic *C. elegans* antigen or control treated mice at 20 weeks of age (9-10 animals per group). Pancreatic islets were classified as non-infiltrated, periinsulitis, and intrainsulitis with less than or more than 50% infiltrated lymphocytes. Statistical significance between groups was assessed by the Mann-Whitney test (*<0.05).
Figure 2B:
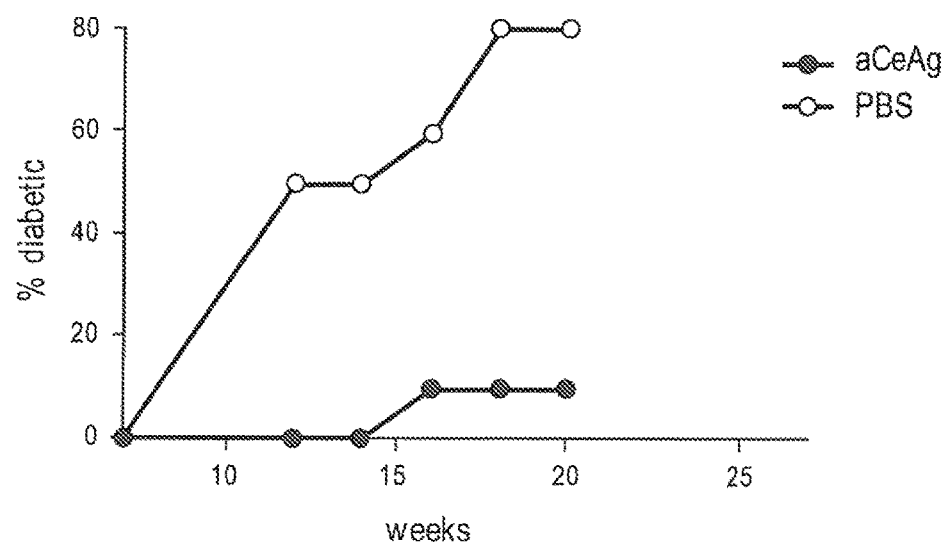
Figure 2C:
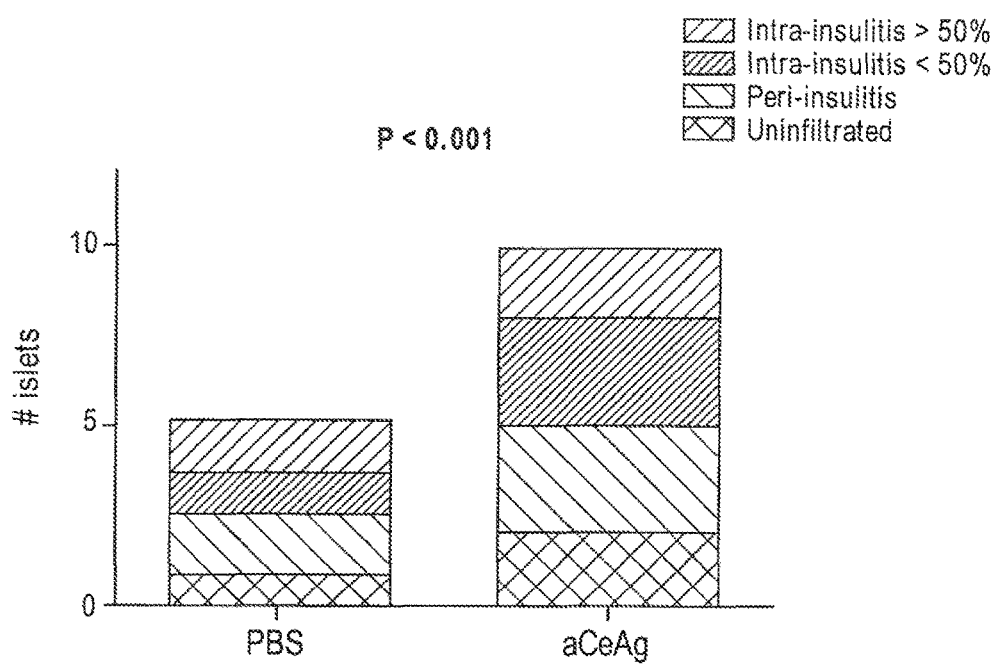

Example 1: Axenic *C. elegans* Antigen Protects Against Type 1 Diabetes in NOD Mice To test the hypothesis that aCeAg can protect against autoimmune disease, development of type I diabetes was monitored in NOD mice that were given repeated aCeAg injections. Repeated administration of aCeAg significantly reduced blood glucose concentrations in NOD mice at 20 weeks of age compared to control animals (FIG. 3A) and delayed the onset of diabetes (80% mice diabetic at 20 wks of age in control group vs 10% in aCeAg group, FIG. 1B). Histological analysis of the pancreas revealed that mice treated with aCeAg mice had greater total numbers of β-islet cells and less lymphocyte infiltration of the pancreatic islets compared to PBS-treated mice at study endpoint (FIG. 2).

Figure 3A:
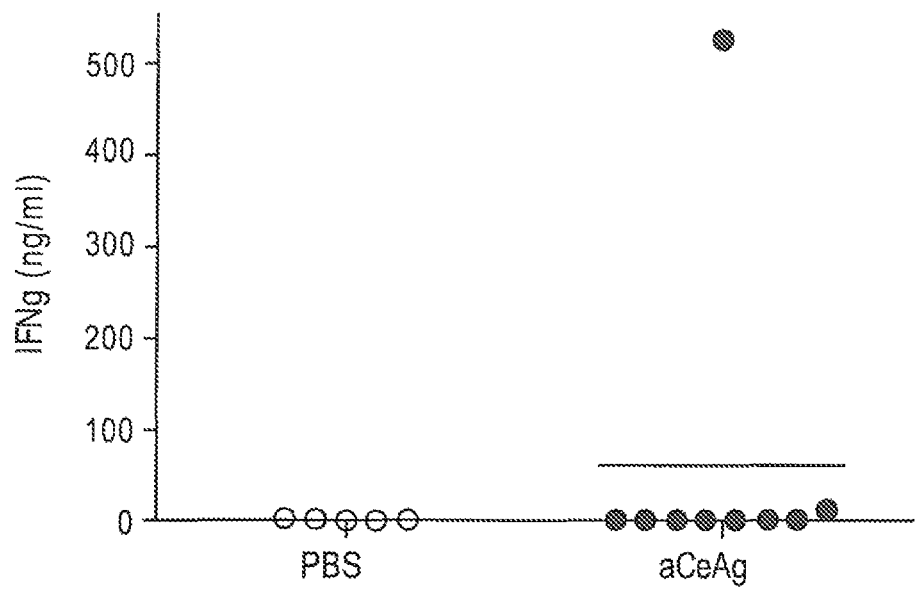
FIGS. 3A-D: Cytokine and antibody response after 10 weeks of axenic *C. elegans* antigen/control treatment at 20 weeks of age. (A) IFNγ and (B) IL-10 cytokine production from spleen cells after in vitro stimulation with 20 µg/ml axenic *C. elegans* antigen. (C) Plasma levels of polyclonal IgE and (D) axenic *C. elegans* antigen-specific IgE. Statistical significance between groups was assessed by the Mann-Whitney test.
Figure 3B:
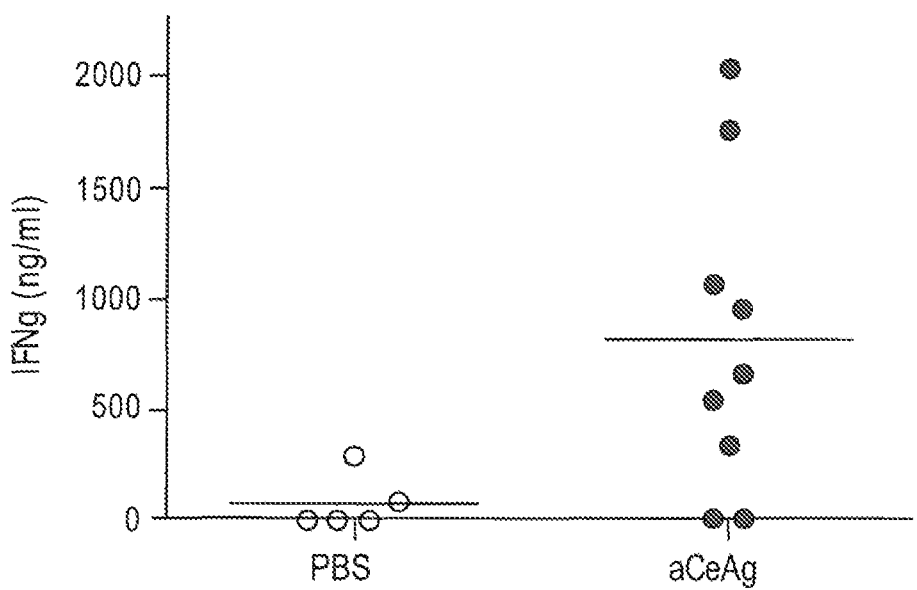
Figure 3C:
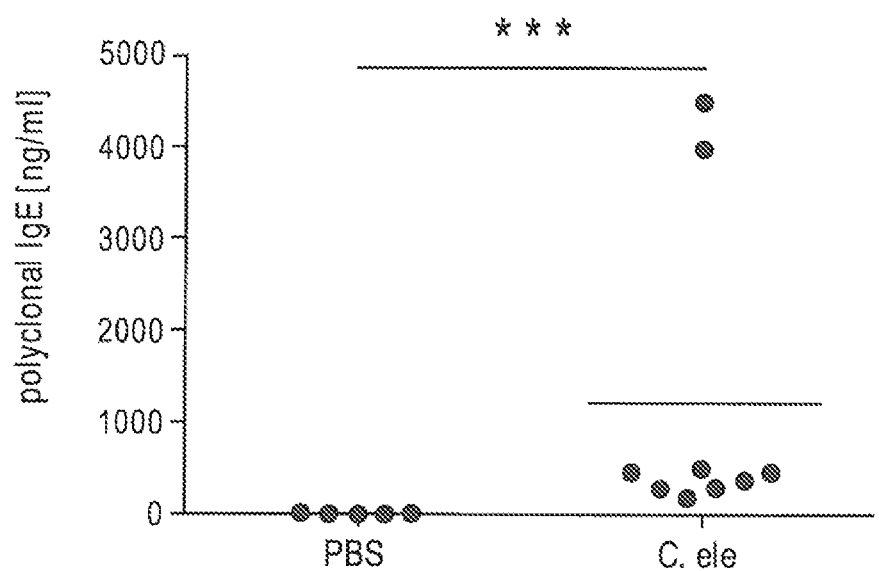
Figure 3D:
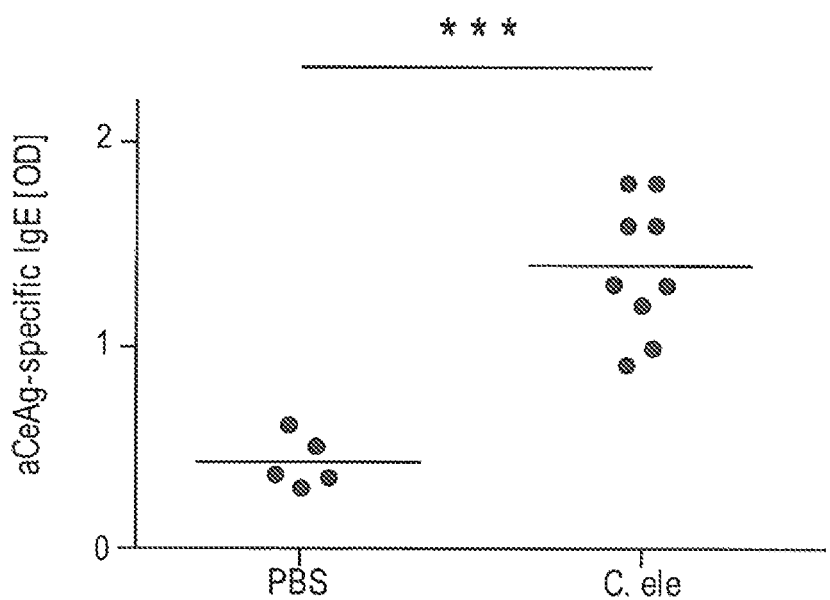

Example 2: Axenic *C. elegans* Antigen Induces Immunological Changes Similar to Those Observed in Response to Helminth Infection Helminth infections characteristically induce increased levels of eosinophils, basophils, and IgE antibodies. To determine whether aCeAg injections induce these changes, at study endpoint levels of circulating eosinophils and basophils were quantified by flow cytometry and plasma total (polyclonal) IgE and aCeAg-specific IgE levels measured by ELISA. Both eosinophil (4.5% in aCeAg treated mice vs 3.1% in NOD mice) and basophil (0.60% vs 0.37%) were increased in mice given aCeAg injections, though the difference was only statistically significant for basophils (FIG. 3A, 3B). Similarly, total and aCeAg-specific IgE levels were also markedly greater in aCeAg-treated mice than controls (FIG. 3C, 3D).

Figure 4:
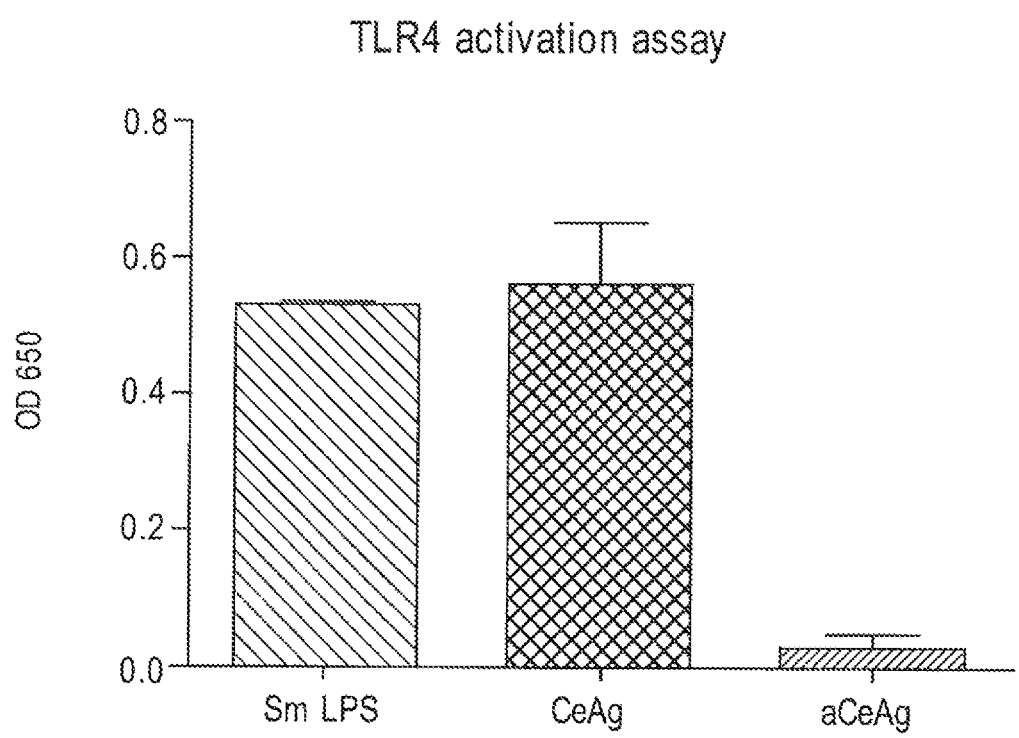
FIG. 4: TLR4 activation in response to LPS, *C. elegans* antigen, and axenic *C. elegans* antigen. TLR4 activation by 10 ng/ml of purified *Salmonella* lipopolysaccharide (positive control), 20 µg/ml *C. elegans* antigen prepared from *C. elegans* grown with OP50 *Escherichia coli*, and 20 µg/ml axenic *C. elegans* antigen. TLR4 activation was determined using an HEK293 cell line (obtained from Invivogen) expressing TLR4 in which a secreted alkaline phosphatase gene under the control of an NF-kB promoter is expressed when TLR4 is activated.

Example 3: Axenic *C. elegans* Antigen Induces Production of IL-10 from Splenocytes The effect repeated aCeAg injections have on cellular cytokine production was evaluated from spleen cells of 20 week old NOD mice after stimulation with aCeAg in vitro. While IL-4 and IL-13 production levels were below the level of detection (data not shown), IL-10 levels were significantly greater from splenocytes of aCeAg-treated NOD mice (FIG. 4A). As IL-10 is a an immunosuppressive cytokine, it is possible that some of the protective effect conferred by aCeAg injections is due to induction of host IL-10 production. IFNγ levels were similar between control and aCeAg-treated animals (FIG. 4B).

Example 4: Axenic *C. elegans* Antigen does not Activate TLR4

*C. elegans* nematode worms are typically grown on a culture plate using *E. coli* bacteria (strain OP-50) as a food source. The limitation to that approach for the purpose of making soluble worm antigen is that the final product will be a mixture of bacterial and worm products. Of particular concern is the *E. coli* product lipopolysaccharide (LPS), which interacts with TLR4 receptors on human cells to induce immediate inflammatory responses. To evaluate whether soluble antigen produced from axenically grown *C. elegans* worms is free of pro-inflammatory TLR-4 activating substances, we tested the ability of aCeAg to activate TLR4 using a reporter cell line for TLR4 activation. In contrast to purified *Salmonella* lipopolysaccharide (positive control) and soluble antigen derived from *C. elegans* worms grown with OP-50 *E. coli*, aCeAg does not induce TLR4 activation.

Unless otherwise defined, all technical and scientific terms used herein have the same meaning as commonly understood by one of ordinary skill in the art. In case of conflict, the present specification, including definitions, will control. It will be readily apparent to one of ordinary skill in the relevant arts that other suitable modifications and adaptations to the methods and applications described herein are obvious and may be made without departing from the scope of the invention or any embodiment thereof. In addition, the materials, methods, and examples are illustrative only and not intended to be limiting. All patents, patent applications, and published references cited herein are hereby incorporated by reference in their entirety.

1. Szewczyk, N. J., E. Kozak, and C. A. Conley, *Chemically defined medium and Caenorhabditis elegans*. BMC Biotechnol, 2003. 3: p. 19.

What is claimed:

1. A method of increasing levels of IgE antibody in a subject, the method comprising administering to the subject an effective amount of a composition comprising a homogenate of *C. elegans*, wherein the homogenate is obtained from *C. elegans* cultured in axenic media that is free of *E. coli*.

2. A method of increasing levels of IL-10 in a subject, the method comprising administering to the subject an effective amount of a composition comprising a homogenate of *C. elegans*, wherein the homogenate is obtained from *C. elegans* cultured in axenic media that is free of *E. coli*.

3. The method of claim 1, wherein the subject is a mammal.

4. The method of claim 1, wherein the subject is a human.

5. The method of claim 1, wherein the composition is administered chronically to the subject.

6. The method of claim 1, wherein the composition is administered orally, parentally, or subcutaneously.

7. The method of claim 1, wherein the composition is free of *E. coli* endotoxins.

8. The method of claim 1, wherein the composition is free of lipopolysaccharides.

9. The method of claim 2, wherein the subject is a mammal.

10. The method of claim 2, wherein the subject is a human.

11. The method of claim 2, wherein the composition is administered chronically to the subject.

12. The method of claim 2, wherein the composition is administered orally, parentally, or subcutaneously.

13. The method of claim 2, wherein the composition is free of *E. coli* endotoxins.

14. The method of claim 2, wherein the composition is free of lipopolysaccharides.

* * * * *